(12) United States Patent
Werling et al.

(10) Patent No.: US 11,787,776 B2
(45) Date of Patent: Oct. 17, 2023

(54) METHOD FOR PRODUCING AN AROMATIC DIANHYDRIDE

(71) Applicant: SHPP Global Technologies B.V., Bergen op Zoom (NL)

(72) Inventors: Robert John Werling, Mt. Vernon, IN (US); Simon Padmanabhan, Mt. Vernon, IN (US); Aaron Matthew Royer, Mt. Vernon, IN (US); Bradley Osborne, Mt. Vernon, IN (US); Christopher Poirier, Mt. Vernon, IN (US)

(73) Assignee: SHPP GLOBAL TECHNOLOGIES B.V., Bergen op Zoom (NL)

( * ) Notice: Subject to any disclaimer, the term of this patent is extended or adjusted under 35 U.S.C. 154(b) by 391 days.

(21) Appl. No.: 15/733,944

(22) PCT Filed: Jun. 4, 2019

(86) PCT No.: PCT/US2019/035325
§ 371 (c)(1),
(2) Date: Dec. 1, 2020

(87) PCT Pub. No.: WO2019/236536
PCT Pub. Date: Dec. 12, 2019

(65) Prior Publication Data
US 2021/0230133 A1 Jul. 29, 2021

(30) Foreign Application Priority Data

Jun. 4, 2018 (EP) ..................................... 18175817

(51) Int. Cl.
*C07D 307/89* (2006.01)
*C07D 407/12* (2006.01)
*C07D 407/10* (2006.01)

(52) U.S. Cl.
CPC ......... *C07D 307/89* (2013.01); *C07D 407/10* (2013.01); *C07D 407/12* (2013.01)

(58) Field of Classification Search
CPC ... C07D 407/12; C07D 407/10; C07D 307/89
See application file for complete search history.

(56) References Cited

U.S. PATENT DOCUMENTS

| | | |
|---|---|---|
| 3,389,970 A | 6/1968 | Scheibel |
| 3,875,116 A | 4/1975 | Heath et al. |
| 3,956,320 A | 5/1976 | Heath et al. |
| 4,020,089 A | 4/1977 | Markezich |
| 4,116,980 A | 9/1978 | Webb |
| 4,217,281 A | 8/1980 | Markezich et al. |
| 4,257,953 A | 3/1981 | Williams, III et al. |
| 4,318,857 A | 3/1982 | Webb et al. |
| 4,329,291 A | 5/1982 | Webb et al. |
| 4,329,292 A | 5/1982 | Webb |
| 4,329,496 A | 5/1982 | Webb |
| 4,340,545 A | 7/1982 | Webb et al. |
| 4,417,044 A | 11/1983 | Parekh |
| 4,520,204 A | 5/1985 | Evans |
| 4,571,425 A | 2/1986 | Silva |
| 4,584,388 A | 4/1986 | Webb |
| 4,902,809 A | 2/1990 | Groeneweg et al. |
| 5,359,084 A | 10/1994 | Dellacoletta et al. |
| 6,008,374 A | 12/1999 | Dellacoletta et al. |
| 6,235,866 B1 | 5/2001 | Khouri et al. |
| 6,265,521 B1 | 7/2001 | Fyvie et al. |
| 6,498,224 B1 | 12/2002 | Odle et al. |
| 7,153,394 B2 | 12/2006 | Guggenheim et al. |
| 10,407,397 B2 | 9/2019 | Royer et al. |
| 2006/0205958 A1 | 9/2006 | Brunelle et al. |
| 2009/0056793 A1 | 3/2009 | Langhals et al. |
| 2009/0247727 A1 | 10/2009 | Bernabe et al. |

(Continued)

FOREIGN PATENT DOCUMENTS

| | | |
|---|---|---|
| CN | 102631794 A | 8/2012 |
| DE | 3213166 A1 | 10/1983 |

(Continued)

OTHER PUBLICATIONS

Basosca, I. et al., "Comparative study of polyimides containing different flexible linkages", J. Iran Chem. Soc., vol. 9, 2012; pp. 901-910.
Bruma, M. et al., "Polyetherimides for Gas Separation Membranes", Molecular Crystals and Liquid Crystals, vol. 418, pp. 11-19.
Hu, Yu Lin et al., "An inexpensive and efficient synthetic method for the preparation of pyromellitic dianhydride promoted by ionic liquid", Arkivoc, vol. 9, 2010; pp. 63-74.
International Search Report for the corresponding International Application No. PCT/US2019/035325; International Filing Date: Jun. 4, 2019; dated Jul. 24, 2019. 6 pages.
Pinzow, Leonard, "Characteristics of a pulsed packed, liquid-liquid extraction column", Calhoun: The NPS Institutional Archive, Retrieved from the Internet on Sep. 20, 2018; http://hdl.handle.net/10945/13989; Jan. 1, 1957; pp. 1-105.
Rauber, Johannes, "Design Practice for Packed Liquid Liquid Extraction Columns", Sulzer, Retrieved from the Internet on Sep. 20, 2018; http://folk.ntnu.no/skoge/prost/proceedings/aiche-2006/data/papers/P73337.pdf Jan. 1, 2006; pp. 1-12.

(Continued)

*Primary Examiner* — Matthew P Coughlin
(74) *Attorney, Agent, or Firm* — CANTOR COLBURN LLP

(57) ABSTRACT

A method for producing an aromatic dianhydride includes reacting an aromatic diimide with a substituted or unsubstituted phthalic anhydride in an aqueous medium in the presence of an amine exchange catalyst to provide an aqueous reaction mixture including an N-substituted phthalimide, an aromatic tetraacid salt, and at least one of an aromatic triacid salt and an aromatic imide diacid salt. The method further includes removing the phthalimide from the aqueous reaction mixture by extracting the aqueous reaction mixture with an organic solvent and converting to the corresponding aromatic dianhydride. The extracting is carried out in an extraction column including a high specific surface area metal packing material and having an interface between the aqueous reaction mixture and the organic solvent that is at a level that is 14 to 85% of the height of the extraction column.

14 Claims, 2 Drawing Sheets

(56) References Cited

U.S. PATENT DOCUMENTS

| | | |
|---|---|---|
| 2011/0319620 A1 | 12/2011 | Ishihara et al. |
| 2019/0040201 A1 | 2/2019 | Patil et al. |
| 2019/0092726 A1 | 3/2019 | Schulte, II et al. |
| 2019/0119240 A1 | 4/2019 | Royer et al. |
| 2019/0135750 A1 | 5/2019 | Croll et al. |
| 2021/0179593 A1 | 6/2021 | Padmanabhan et al. |
| 2021/0246124 A1 | 8/2021 | Royer et al. |

FOREIGN PATENT DOCUMENTS

| | | | |
|---|---|---|---|
| EP | 0477539 A1 | 4/1992 | |
| WO | 2017172593 A1 | 5/2017 | |
| WO | 2017189293 A1 | 11/2017 | |
| WO | WO-2017189293 A1 * | 11/2017 | ........... C07D 307/89 |

OTHER PUBLICATIONS

Schwartz, W. T., "A Novel Route to Aryl Diether Dianhydrides", High Performance Polymers, vol. 2, No. 3, 1990 pp. 189-196.

Wei, Haibing et al., "Comparative Study on Polyimides from Isomeric 3,3'-, 3,4'-, and 4,4'- Linked Bis(thioether anhydride)s", Journal of Polymer Science Part A: Polymer Chemistry, vol. 49, 2011; pp. 2484-2494.

Written Opinion or the corresponding International Application No. PCT/US2019/035325; International Filing Date: Jun. 4, 2019; dated Jul. 24, 2019. 6 pages.

Yoon, Chong-Bok et al., "Facile synthesis of new NLO-functionalized polyimides via Mitsunobu reaction", Journal Material Chemistry, vol. 9; 1999; pp. 2339-2344.

International Search Report for the corresponding International Application No. PCT/US2019/030810; International Filing Dtae: May 6, 2019; dated Jul. 30, 2019. 5 pages.

Written Opinion for the corresponding International Application No. PCT/US2019/030810; International Filing Dtae: May 6, 2019; dated Jul. 30, 2019. 9 pages.

International Search Report for International Application No. PCT/US2019/031972; International Filing Date May 13, 2019; dated Jul. 8, 2019; 8 pages.

Written Opinion for International Application No. PCT/US2019/031972; International Filing Date May 13, 2019; dated Jul. 8, 2019; 12 pages.

International Search Report for International Application No. PCT/US2019/037182; International Filing Date Jun. 14, 2019; dated Aug. 26, 2019; 6 pages.

Written Opinion for International Application No. PCT/US2019/037182; International Filing Date Jun. 14, 2019; dated Aug. 26, 2019; 9 pages.

International Search Report for International Application No. PCT/US2017/028263; International Filing Date Apr. 19, 2017; dated Aug. 24, 2017; 6 pages.

Written Opinion of the International Searching Authority for International Application No. PCT/US2017/028263; International Filing Date Apr. 19, 2017; dated Aug. 24, 2017; 9 pages.

* cited by examiner

METHOD FOR PRODUCING AN AROMATIC DIANHYDRIDE

CROSS-REFERENCE TO RELATED APPLICATIONS

This application is a National Stage application of PCT/US2019/035325, filed Jun. 4, 2019, which claims benefit of European Application No. 18175817.8 filed on Jun. 4, 2018.

BACKGROUND

Polyetherimides are a class of high performance polymers that can be processed to make molded articles, fibers, films, foams, and the like. Polyetherimides further have high strength, toughness, heat resistance, modulus, and broad chemical resistance, and so are widely used in industries as diverse as automotive, telecommunication, aerospace, electrical/electronics, transportation, and healthcare. Polyetherimides have shown versatility in various manufacturing processes, proving amenable to techniques including injection molding, extrusion, and thermoforming, to prepare various articles.

A number of processes for making polyetherimides have been disclosed. Two processes which have been of particular interest are the so-called melt polymerization and solution polymerization processes. Solution polymerization is generally conducted by reacting an aromatic dianhydride and an organic diamine in an inert solvent at elevated temperatures to form an amide-acid polymer via ring opening of the anhydride by nucleophilic attack of the diamine. The polyamide-acid is then formed into a polyetherimide by removal of water, for example by azeotropic distillation.

Aromatic dianhydrides are thus important to the production of polyetherimides. The aromatic dianhydrides can be prepared using an exchange reaction between an aromatic bisimide and a substituted or unsubstituted phthalic anhydride. In addition to dianhydride, the exchange reaction often produces various by-products which result in decreased yields of the dianhydride. WO 2017/189293 discloses a method for producing an aromatic dianhydride. The method includes removing phthalimide from the reaction mixture by extraction with an organic solvent.

Accordingly, there remains a need for an improved method for producing and isolating dianhydrides that can provide high yields and minimize by-product formation.

BRIEF DESCRIPTION

A method for producing an aromatic dianhydride comprises reacting an aromatic diimide with a substituted or unsubstituted phthalic anhydride in an aqueous medium in the presence of an amine exchange catalyst under conditions effective to provide an aqueous reaction mixture comprising an N-substituted phthalimide, an aromatic tetraacid salt, and at least one of an aromatic triacid salt and an aromatic imide diacid salt, wherein the reacting is at a reaction temperature that is 140 to 250° C. and a reaction pressure of 1.13 to 2.16 MPa, (150 to 300 psig), preferably 1.48 to 1.82 MPa (200 to 250 psig); removing the phthalimide from the aqueous reaction mixture by extracting the aqueous reaction mixture with an organic solvent; and converting the aromatic tetraacid salt to the corresponding aromatic dianhydride; wherein the extracting is in an extraction column comprising a metal packing material having a specific surface area of greater than 1500 square meters per cubic meter; wherein extracting the aqueous reaction mixture comprises passing a dispersed phase comprising the aqueous reaction mixture through a continuous phase comprising the organic solvent; and wherein an interface between the aqueous reaction mixture and the organic solvent in the extraction column is at a level that is 14 to 85% of the height of the extraction column.

The above described and other features are exemplified by the following figures and detailed description.

DETAILED DESCRIPTION

The present inventors have discovered that the use of a modified extraction procedure for isolation of an aromatic dianhydride can increase the overall dianhydride conversion and yield. In particular, the present inventors have discovered that use of an extraction column having a high specific surface area packing material and performing the extracting in an extraction column having an interface between the aqueous reaction mixture and the organic solvent that is at a specified level of the total height of the extraction column can be advantageous.

Figure 1:
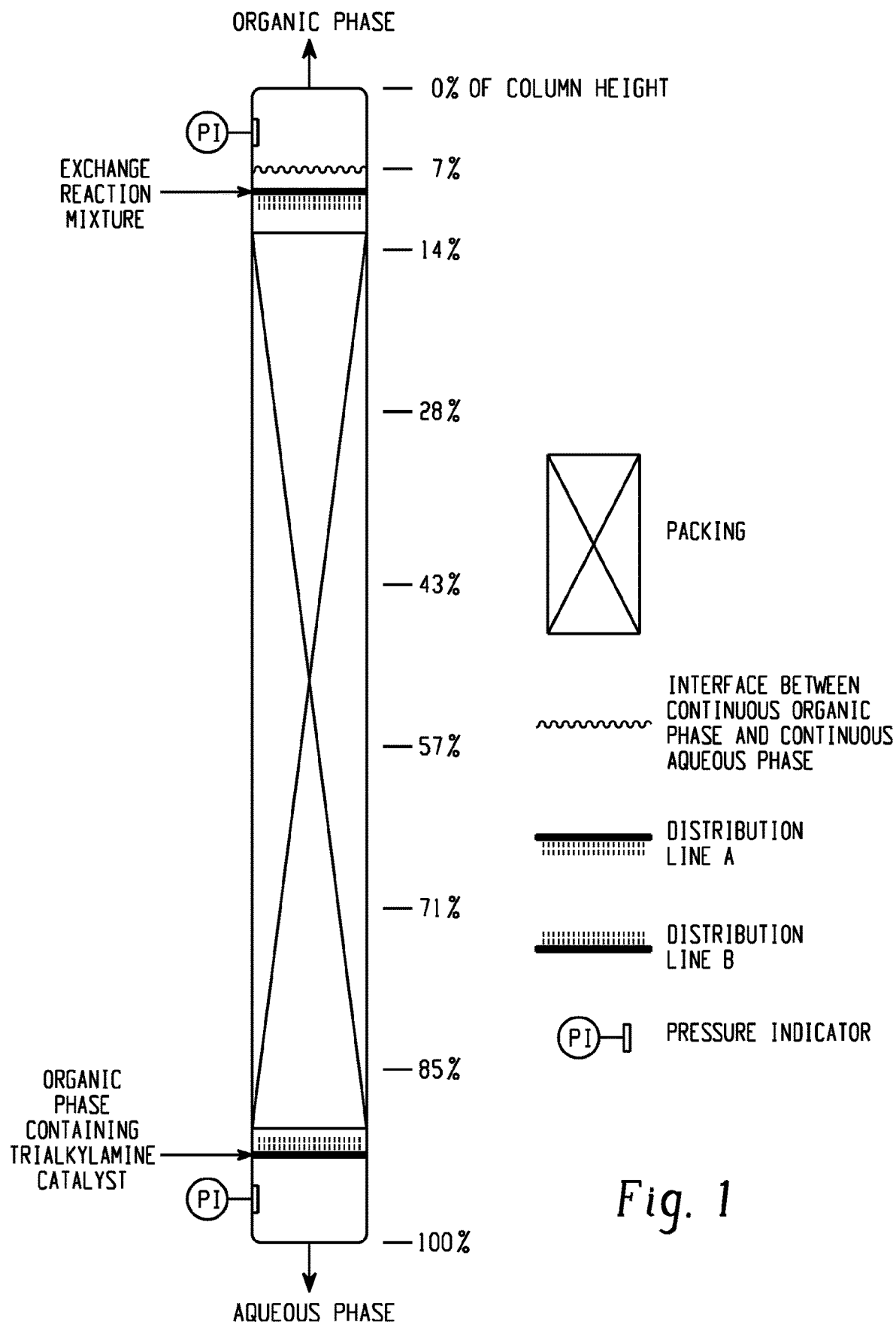
FIG. 1 is a schematic illustration of an extraction column operating at an interface level of 7%.

Conventionally, in an extraction column, there is a continuous phase and a dispersed phase, for example as shown in FIG. 1. During conventional operation, the aqueous phase is continuous and has a specific gravity greater than that of the dispersed organic solvent. Since the organic solvent has a lower specific gravity, it enters the column through a distribution line (distribution line B in FIG. 1), near the bottom of the column. Droplets of the organic solvent rise up through the packing and extract organic soluble components from the aqueous reaction mixture, which enters the column through a distribution line (distribution line A in FIG. 1) above the top of the packing. Above the aqueous distribution line, the organic droplets coalesce and an interface between the aqueous and the organic phase is maintained. If the interface is instead positioned within the column packing, then the number of effective extraction stages is reduced, as typical extraction packings cannot be wetted by the organic phase.

Accordingly, a method for producing an aromatic dianhydride represents an aspect of the present disclosure. The method comprises reacting an aromatic diimide (also referred to as an "aromatic bisimide" or "bisimide") with a substituted or unsubstituted phthalic anhydride in an aqueous medium in the presence of an amine exchange catalyst and under conditions effective to provide an aqueous reaction mixture.

The aromatic bisimide can be of the formula (1)

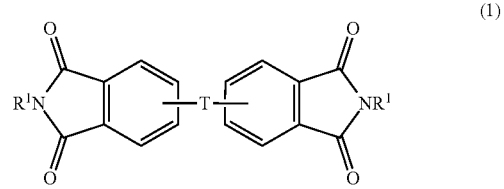

wherein T is —O—, —S—, —C(O)—, —SO$_2$—, —SO—, —C$_y$H$_{2y}$— wherein y is an integer from 1 to 5 or a halogenated derivative thereof or —O—Z—O—, wherein Z is an aromatic C$_{6-24}$ monocyclic or polycyclic moiety optionally substituted with 1 to 6 C$_{1-8}$ alkyl groups, 1 to 8 halogen atoms, or a combination comprising at least one of the foregoing. In an aspect, R$^1$ is a monovalent C$_{1-13}$ organic group.

In an aspect, T is —O— or a group of the formula —O—Z—O— wherein the divalent bonds of the —O— or the —O—Z—O— group are in the 3,3', 3,4', 4,3', or the 4,4' positions. Exemplary groups Z include groups of formula (2)

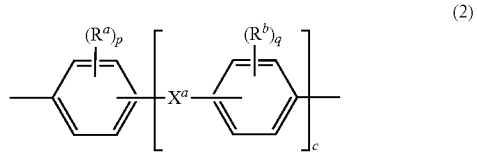

(2)

wherein R$^a$ and R$^b$ are each independently the same or different, and are a halogen atom or a monovalent C$_{1-6}$ alkyl group, for example; p and q are each independently integers of 0 to 4; c is 0 to 4; and X$^a$ is a bridging group connecting the hydroxy-substituted aromatic groups, where the bridging group and the hydroxy substituent of each C$_6$ arylene group are disposed ortho, meta, or para (specifically para) to each other on the C$_6$ arylene group. The bridging group X$^a$ can be a single bond, —O—, —S—, —S(O)—, —S(O)$_2$—, —C(O)—, or a C$_{1-18}$ organic bridging group. The C$_{1-18}$ organic bridging group can be cyclic or acyclic, aromatic or non-aromatic, and can further comprise heteroatoms such as halogens, oxygen, nitrogen, sulfur, silicon, or phosphorous. The C$_{1-18}$ organic group can be disposed such that the C$_6$ arylene groups connected thereto are each connected to a common alkylidene carbon or to different carbons of the C$_{1-18}$ organic bridging group. A specific example of a group Z is a divalent group of the formula (3a) or (3b)

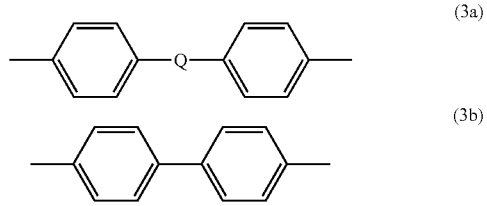

(3a)

(3b)

wherein Q is —O—, —S—, —C(O)—, —SO$_2$—, —SO—, —P(R$^a$)(=O)— wherein R$^a$ is a C$_{1-8}$ alkyl or C$_{6-12}$ aryl, or —C$_y$H$_{2y}$— wherein y is an integer from 1 to 5 or a halogenated derivative thereof (including a perfluoroalkylene group). Exemplary dihydroxy aromatic compounds from which Z can be derived include but are not limited to 2,2-bis(2-hydroxyphenyl)propane, 2,4'-dihydroxydiphenylmethane, bis(2-hydroxyphenyl)methane, 2,2-bis-(4-hydroxyphenyl)propane ("bisphenol A" or "BPA"), 1,1-bis-(4-hydroxyphenyl)ethane, 1,1-bis-(4-hydroxyphenyl)propane, 2,2-bis-(4-hydroxyphenyl)pentane, 3,3-bis-(4-hydroxyphenyl)pentane, 4,4'-dihydroxybiphenyl, 4,4'-dihydroxy-3,3,5,5'-tetramethylbiphenyl, 2,4'-dihydroxybenzophenone, 4,4'-dihydroxydiphenylsulfone, 2,4'-dihydroxydiphenylsulfone, 4,4'-dihydroxydiphenylsulfoxide, 4,4'-dihydroxydiphenylsulfide, hydroquinone, resorcinol, 3,4-dihydroxydiphenylmethane, 4,4'-dihydroxybenzophenone, 4,4'-dihydroxydiphenylether, and the like, or a combination comprising at least one of the foregoing. In a specific embodiment, Z is derived from bisphenol A, such that Q in the above formula is, 2,2-isopropylidene. Thus in an aspect, Z is 2,2-(4-phenylene)isopropylidene. In an aspect, R$^1$ is a C$_{1-4}$ alkyl group, for example a methyl group, an ethyl group, a propyl group, or a butyl group, preferably a methyl group.

In an aspect, the aromatic bisimide comprises 4,4'-bisphenol A-bis-N-methylphthalimide, 3,4'-bisphenol A-bis-N-methylphthalimide, 3,3'-bisphenol A-bis-N-methylphthalimide, or a combination comprising at least one of the foregoing.

The substituted or unsubstituted phthalic anhydride can be of the formula (4)

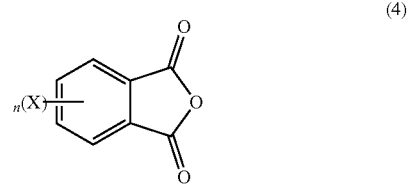

(4)

wherein X is fluoro, chloro, bromo, iodo, nitro, or a combination comprising at least one of the foregoing, and n is 0 or 1. In an aspect, n is 0 and the phthalic anhydride is an unsubstituted phthalic anhydride. In an aspect, n is 1, and the phthalic anhydride is a substituted phthalic anhydride, wherein X is fluoro, chloro, bromo, iodo, nitro, or a combination comprising at least one of the foregoing. In an aspect, the substituted or unsubstituted phthalic anhydride comprises phthalic anhydride, 3-halophthalic anhydride, 4-halophthalic anhydride, 3-nitrophthalic anhydride, 4-nitrophthalic anhydride, or a combination comprising at least one of the foregoing. Specific examples of suitable halophthalic anhydrides include 3-fluorophthalic anhydride, 4-fluorophthalic anhydride, 3-chlorophthalic anhydride, 4-chlorophthalic anhydride, 3-bromophthalic anhydride, 4-bromophthalic anhydride, 3-iodophthalic anhydride, and 4-iodophthalic anhydride. In an embodiment, the substituted or unsubstituted phthalic anhydride is preferably phthalic anhydride.

Reacting the aromatic bisimide with the substituted or unsubstituted phthalic anhydride is carried out in aqueous medium in the presence of an amine exchange catalyst. The amine exchange catalyst can include a (C$_{1-20}$ alkyl)-substituted amine, preferably a tri(C$_{1-20}$ alkyl)amine. In an aspect, the amine exchange catalyst is preferably triethylamine. In an aspect, the initial molar ratio of amine exchange catalyst to the phthalic anhydride is 1:1 to 2:1.

The reacting is further carried out under conditions effective to provide an aqueous reaction mixture. Effective conditions can include reacting at a reaction temperature that is 140 to 250° C., for example 160 to 200° C., and a reaction pressure of 150 to 300 psig (1.13 to 2.16 megapascals (MPa)), preferably 200 to 250 psig (1.48 to 1.82 MPa), more preferably 200 to 230 psig (1.48 to 1.68 MPa).

In an aspect, the initial molar ratio of phthalic anhydride to aromatic bisimide is 4:1 to 20:1, or 4:1 to 10:1, or 4:1 to 8:1, or 4:1 to 5.5:1, or 4:1 to 5.5:1. Without wishing to be bound by theory, it is believed that a molar ratio of phthalic anhydride to aromatic bisimide of 4:1 to 5:1 can be preferred at least for economic reasons.

The aqueous reaction mixture provided by reacting the aromatic bisimide with the substituted or unsubstituted phthalic anhydride comprises an N-substituted phthalimide, an aromatic tetraacid salt, and at least one of an aromatic triacid salt and an aromatic imide diacid salt. The N-substituted phthalimide can be an N—($C_{1-13}$ alkyl) substituted phthalimide, preferably an N—($C_{1-6}$ alkyl) substituted phthalimide, for example N-methyl phthalimide.

In an aspect, the aromatic tetra acid salt is of the formula (5)

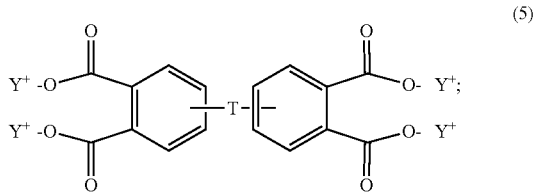

the aromatic triacid salt is of the formula (6)

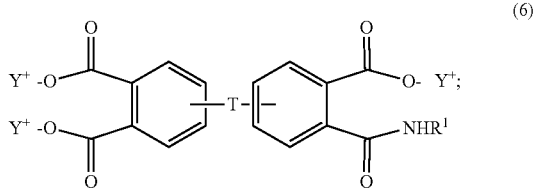

and
the aromatic imide-diacid salt is of the formula (7)

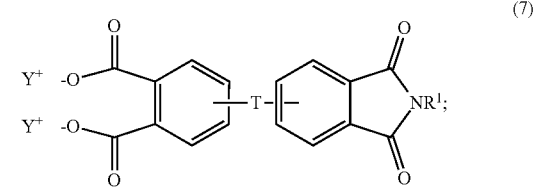

wherein T can be as described above, and is preferably —O—, —S—, —C(O)—, —$SO_2$—, —SO—, —$C_yH_{2y}$— wherein y is an integer from 1 to 5 or a halogenated derivative thereof or —O—Z—O—, wherein Z is an aromatic $C_{6-24}$ monocyclic or polycyclic moiety optionally substituted with 1 to 6 $C_{1-8}$ alkyl groups, 1 to 8 halogen atoms, or a combination comprising at least one of the foregoing, $R^1$ is a $C_{1-13}$ organic group, or a $C_{1-4}$ alkyl group, preferably a methyl group, and Y is a cationic group, preferably a $C_{1-20}$ trialkylammonium group (i.e., an aromatic tetraacid ammonium salt, triacid ammonium salt, and imide diacid ammonium salt), or a proton (i.e., the aromatic tetraacid ammonium salt, triacid ammonium salt, and imide diacid ammonium salt can be in the form of the corresponding aromatic tetraacid, triacid, and imide acid, respectively). In an aspect, Y is a $C_{1-20}$ trialkylammonium group, preferably a triethylammonium group. Thus, in an aspect, the aromatic tetra acid salt can be an aromatic tetra acid triethylamine salt, the aromatic triacid salt can be an aromatic triacid triethylamine salt, and the aromatic imide-diacid salt can be an aromatic imide-diacid triethylamine salt. In an aspect, T is —O—Z—O—, wherein Z is derived from bisphenol A. The divalent bonds of the —O—Z—O— group are in the 3,3', 3,4', 4,3', or the 4,4' positions.

In an aspect, the aqueous reaction mixture can further comprise at least one of the aromatic bisimide and the substituted or unsubstituted phthalic anhydride. In an aspect, the aqueous reaction mixture can further comprise the substituted or unsubstituted phthalic anhydride, preferably wherein the substituted or unsubstituted phthalic anhydride is in the form of the corresponding ring-opened diacid salt, for example a corresponding ring-opened diacid $C_{1-20}$ trialkylammonium salt.

The method further comprises removing the N-substituted phthalimide and any residual aromatic bisimide from the aqueous reaction mixture by extracting the aqueous reaction mixture with an organic solvent. In an aspect, the organic solvent is a ($C_{1-6}$ alkyl)benzene, benzene, or a halogenated aromatic solvent. For example, the organic solvent can comprise toluene, xylene, chlorobenzene, ortho-dichlorobenzene, or a combination comprising at least one of the foregoing. In some embodiments, the organic solvent can optionally comprise 0 to 15 weight percent, or 1 to 10 weight percent, or 2 to 8 weight percent of a tri($C_{1-6}$ alkyl)amine, preferably triethylamine. In an aspect, the volumetric ratio of the organic solvent to the aqueous medium is 1:1 to 3:1, or 1.05:1 to 2.5:1, or 1.1:1 to 2:1.

The extracting to remove the N-substituted phthalimide and any residual aromatic bisimide is in an extraction column. When using an extraction column, the aqueous phase from the exchange reaction is typically fed into the top of the extraction column while the organic solution is fed into the bottom of the exchange column, as shown in FIGS. 1 and 2.

Figure 2:
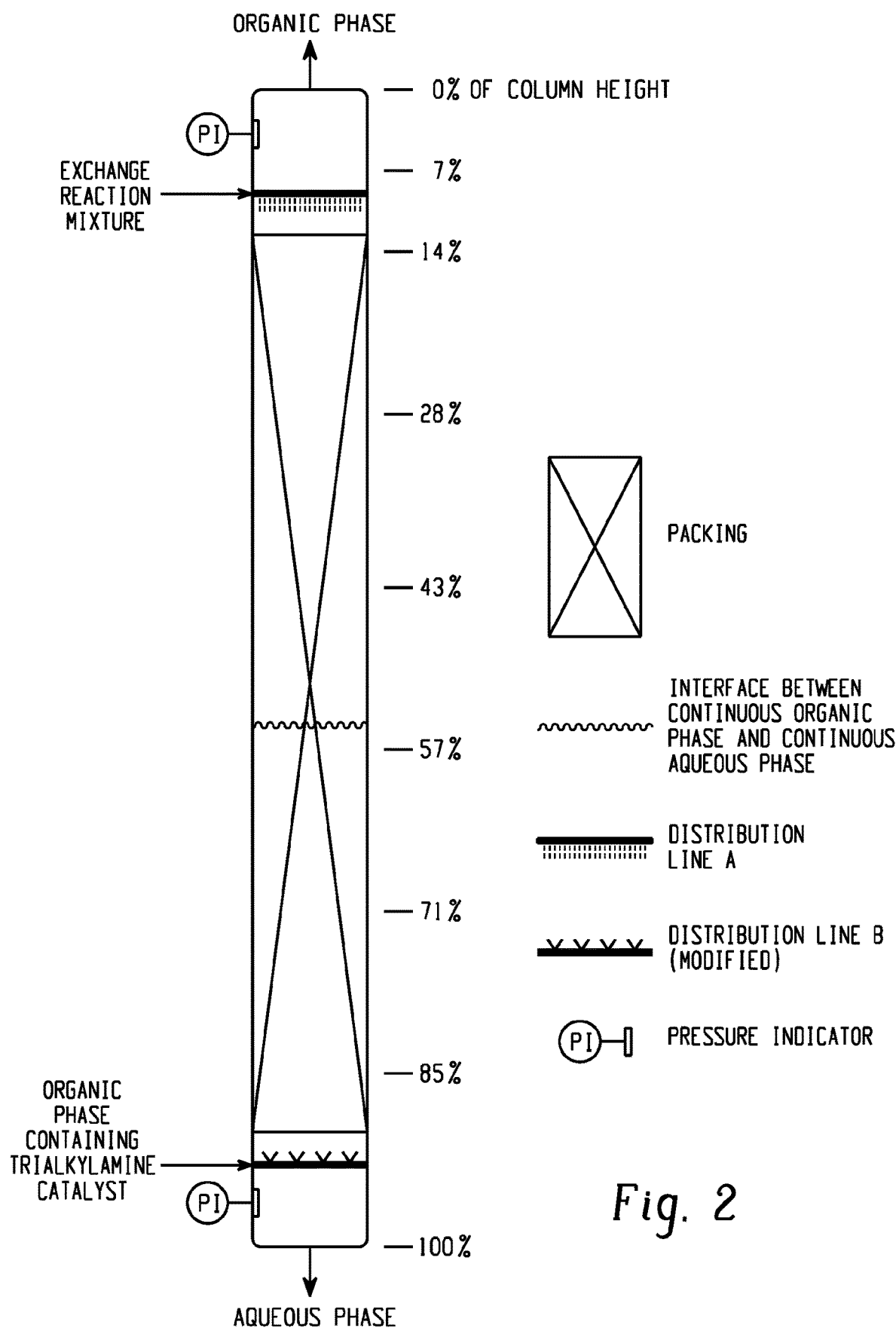
FIG. 2 is a schematic illustration of an extraction column operating according to an aspect of the present disclosure.

The present inventors unexpectedly found that moving the interface between the organic phase and the aqueous phase between the respective distributors and within the packing of the column, for example as shown in FIG. 2, increased the effective number of stages and was found to improve extraction efficiency, afford higher purity product (i.e., aromatic dianhydride), increase capacity, and increase first pass yield. This is further described in the working examples below, where an interface at 27, 40 or 55% of the total column height provided improved results compared to an interface at 7% of the total column height. As used herein, "column height" is to be interpreted as shown in the Figures, where 0% of the column height refers to the top of the extraction column, and 100% column height refers to the bottom of the extraction column. The interface also advantageously is positioned within the packing of the column.

The extracting comprises passing the aqueous reaction mixture as a dispersed phase through the organic solvent as a continuous phase in the top of the column, maintaining the interface between the organic phase and aqueous phase within a desired height of the column, and passing the organic solvent as a dispersed phase through the aqueous reaction mixture as a continuous phase in the bottom of the column. The dispersed aqueous phase can be in the form of, for example, bubbles, droplets, rivulets, films, or the like, or a combination thereof. The present inventors unexpectedly determined that carrying out the extraction with the aqueous reaction mixture as the dispersed phase and the organic solvent as the continuous phase in the top portion of the column (in contrast to typical processes in which the aqueous reaction mixture is the continuous phase and the organic solvent is the dispersed phase) allows for increased extraction efficiency of the desired aromatic dianhydride product, improved conversion of imide-anhydride intermediate to the corresponding tetraacid, with increased capacity.

The present inventors have discovered extracting in an extraction column having an interface between the aqueous reaction mixture and the organic solvent that is at a level that is 14 to 85% of the height of the extraction column can be advantageous. The interface also resides within the column packing. Preferably, the interface between the aqueous reaction mixture and the organic solvent is lower than the inlet which conveys the aqueous reaction mixture to the extraction column, also referred to herein as the distribution line (in contrast to typical processes in which the interface between the aqueous reaction mixture and the organic solvent is above the inlet which conveys the aqueous reaction mixture to the extraction column). This unexpectedly led to improved extraction efficiency and conversion of imide anhydride to the tetraacid. Within the range of 14 to 85%, the interface between the aqueous reaction mixture and the organic solvent can be at least 14, or 20, or 30, or 35, or 40, or 45, or 50% of the height of the extraction column. Also within this range, the interface between the aqueous reaction mixture and the organic solvent can be at most 85, or 80, or 75, or 70, or 60% of the height of the extraction column. In an aspect, the interface can be at a level of 40 to 70%, or 45 to 65%, or 50 to 60% of the total column height.

The extraction column includes a high specific surface area packing material. Preferably the packing material comprises metal. For example, the packing material can comprise stainless steel, titanium, zirconium, aluminum, iron, and the like, as well as alloys thereof, preferably stainless steel. More preferably, the packing materials is a metal structured packing material. The packing material can be a woven packing material, for example, Goodloe packing, Koch-Sulzer packing, Neo Koss packing, Leva film trays packing, and the like. Advantageously the woven packing used is Goodloe packing. This packing is typically made of 0.0045 in. diameter wires, with 12 strands being knitted together to form a tube. The tube is flattened to make a double-thickness ribbon approximately 6 inches wide. This ribbon is crimped, the creases of the crimping being at an angle to the centerline of the ribbon. The ribbons are then arranged in reversed relationship so that the creases cross each other, thereby determining the spacing of the adjacent ribbons. The two ribbons are rolled together until a cartridge is formed having enough layers to provide a diameter to fit inside the column snugly. Goodloe packing as used and described herein is available from Koch-Glitsche.

In an aspect, the packing material can further comprise a non-metal packing material. For example, the packing material can be a knitted wire mesh packing material comprising a non-metal component, for example a polymeric component.

The packing material can have a specific surface area of greater than 1500 square meters per cubic meter, greater than 1500 to 20000 square meters per cubic meter, or 1750 to 18000 square meters per cubic meter, or 1900 to 17500 square meters per cubic meter, or 1970 to 16400 square meters per cubic meter.

The extracting can be carried out for a period of time of, for example, 30 seconds to 3 hours, or 5 minutes to 3 hours, or 20 minutes to 3 hours, or 20 minutes to 2 hours, or 20 minutes to 1 hour, or 1 to 3 hours, or 1 to 2 hours, or 1 to 1.5 hours, preferably 5 minutes to 3 hours, or 20 minutes to 2 hours, or 20 minutes to 1 hour. The extracting can be at a temperature of 130 to 250° C., or 145 to 200° C., or 145 to 165° C.

In an aspect, the extracting provides an extracted aqueous stream comprising the aromatic tetraacid salt and optionally the aromatic triacid salt, the aromatic imide-diacid salt, a substituted or unsubstituted phthalic acid salt, or a combination comprising at least one of the foregoing, and an organic stream comprising the organic solvent, N-substituted phthalimide, and optionally residual aromatic bisimide.

In an aspect, the method can further include repeating the extracting in order to provide the desired conversion of the aromatic bisimide to aromatic tetraacid salt, for example greater than 70%, or greater than 75%, or greater than 78%, or greater than 80%. Repeating the extracting can include any number of additional extractions.

In an aspect, the method described herein can provide the aromatic tetraacid salt in a first pass yield of at least 75%, or at least 80%. In an aspect, the desired first pass yield is obtained at a desired bisimide:phthalic anhydride molar ratio and percent solids (also referred to as "solids content"). As used herein, the term "solids content" is defined as the weight of the aromatic bisimide, the aromatic dianhydride, and, when present, the aromatic imide-anhydride, the aromatic tetra acid salt, the aromatic triacid salt, the aromatic imide-diacid salt, and the corresponding ring-closed derivatives thereof, relative to the total weight of the reaction mixture. In an aspect, the aqueous reaction mixture can have a solids content of 5 to 26 weight percent, or 10 to 20 weight percent, or 13 to 23 weight percent, or 13 to 17 weight percent, or 13 to 16 weight percent. Within this range, the solids content can be at least 5, 10, 12, 15, 17, or 18 weight percent. Also within this range, the solids content can be less than or equal to 24, 23, 19, or 16 weight percent.

The method further comprises converting the aromatic tetraacid salt to the corresponding aromatic dianhydride. The amount of time as well as the temperature for the converting is generally dependent upon the identity of the dianhydride and can be readily determined by one of ordinary skill in the art. For example, useful temperatures can be 160 to 300° C., or 180 to 240° C. or 200 to 220° C. The conversion of the aromatic tetraacid salt to dianhydride is a cyclization with the concurrent formation of water and evolution of a free amine species derived from the cationic group Y. The tetraacid salt can be condensed by refluxing in the presence of a dehydrating agent, for example acetic anhydride. In an aspect, a temperature of 100 to 225° C. and a pressure of 0 MPa to 1 MPa can be used. It is also noted that any phthalic anhydride present in the form of the corresponding ring-opened diacid salt present can be converted to phthalic anhydride by cyclization with the concurrent formation of water and evolution of a free amine species derived from the cationic group under the same conditions described above for the conversion of the aromatic tetraacid salt. Advantageously, trace water, catalyst, and other residual volatile materials such as phthalic anhydride can also be removed as vapor under the conditions utilized for conversion. In an aspect, the converting can provide a product mixture comprising the aromatic dianhydride and an aromatic imide-anhydride, for example formed from the cyclization of the above-described aromatic triacid salt.

The aromatic dianhydride can be of the formula (8)

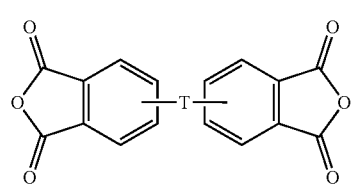

(8)

wherein T can be as defined above. In an aspect, T is —O—Z—O—, preferably wherein Z is derived from bisphenol A (i.e., Z is 2,2-(4-phenylene)isopropylidene). Illustrative examples of aromatic dianhydrides include 3,3-bis[4-(3,4-dicarboxyphenoxy)phenyl]propane dianhydride; 4,4'-bis(3,4-dicarboxyphenoxy)diphenyl ether dianhydride; 4,4'-bis(3,4-dicarboxyphenoxy)diphenyl sulfide dianhydride; 4,4'-bis(3,4-dicarboxyphenoxy)benzophenone dianhydride; 4,4'-bis(3,4-dicarboxyphenoxy)diphenyl sulfone dianhydride; 2,2-bis[4-(2,3-dicarboxyphenoxy)phenyl]propane dianhydride; 4,4'-bis(2,3-dicarboxyphenoxy)diphenyl ether dianhydride; 4,4'-bis(2,3-dicarboxyphenoxy)diphenyl sulfide dianhydride; 4,4'-bis(2,3-dicarboxyphenoxy)benzophenone dianhydride; 4,4'-bis(2,3-dicarboxyphenoxy)diphenyl sulfone dianhydride; 4-(2,3-dicarboxyphenoxy)-4'-(3,4-dicarboxyphenoxy)diphenyl-2,2-propane dianhydride; 4-(2,3-dicarboxyphenoxy)-4'-(3,4-dicarboxyphenoxy)diphenyl ether dianhydride; 4-(2,3-dicarboxyphenoxy)-4'-(3,4-dicarboxyphenoxy)diphenyl sulfide dianhydride; 4-(2,3-dicarboxyphenoxy)-4'-(3,4-dicarboxyphenoxy) benzophenone dianhydride; and, 4-(2,3-dicarboxyphenoxy)-4'-(3,4-dicarboxyphenoxy)diphenyl sulfone dianhydride.

The aromatic imide-anhydride can be of the formula (9)

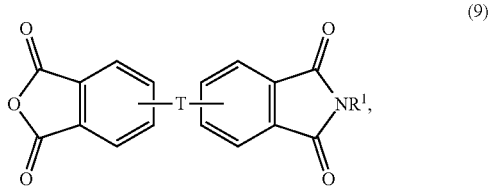

(9)

wherein T and $R^1$ are as defined above. In an aspect, T is —O—Z—O—, wherein Z is derived from bisphenol A. In an aspect, $R^1$ is preferably a methyl group.

In an aspect, overall conversion of the aromatic bisimide to an aromatic dianhydride can be greater than 70%, or greater than 75%, or greater than 78% or greater than 80%. In an aspect, conversion of the aromatic bisimide to aromatic dianhydride can be 70 to 90%, or 75 to 90%, or 78 to 90%, or 80 to 90%, or 80 to 89% or 85 to 89%.

An aromatic dianhydride prepared according to the above-described method is another aspect of the present disclosure. The aromatic dianhydride can be of formula (8) above. In some embodiments, the aromatic dianhydride can have an imide-anhydride content of less than or equal to 6 wt %, preferably less than or equal to 3 wt. %, based on the total weight of the aromatic dianhydride, wherein the imide-anhydride can be according to formula (9) above. The lower limit of the imide-anhydride content is not particularly limited. In an aspect, the lower limit of the imide-anhydride content can be, for example, 0.5%, or 0.75%, or 0.8%, or 1 wt %. This is a particularly advantageous feature of the present disclosure because imide anhydride is a monofunctional reactant from the standpoint of a polymerization to form poly(etherimide). Thus, any imide anhydride present will act as a chain stopper during a polymerization reaction, making it difficult to achieve high molecular weight poly (etherimide). High molecular weight poly(etherimide) can provide many advantages, thus providing a higher purity aromatic dianhydride which in particular includes very low amounts of imide anhydride chain stopper is especially advantageous.

An improved method for isolation of an aromatic dianhydride is thus provided herein. The method advantageously employs extracting using a particular extraction column having a high specific surface area metal packing material and an interface between the aqueous reaction mixture and the organic solvent that is at a level that is 14 to 85% of the height of the extraction column. Such a method can increase overall conversion to dianhydride and increase the yield of the isolated aromatic dianhydride, and provide an increase in capacity. Therefore, a substantial improvement in methods of isolating an aromatic dianhydride is provided.

This disclosure is further illustrated by the following examples, which are non-limiting.

EXAMPLES

As shown in FIG. 2, it has been discovered by the present inventors that by lowering the interface level below the top aqueous distributor in the presence of a high specific surface area packing, the extraction efficiency of the imide species, primarily N-methyl phthalimide, can be improved along with the conversion efficiency and production capacity of aromatic bisimide to the tetraacid species. This was a surprising result because toluene (used as the organic solvent in the present Examples) does not preferentially wet metal packing material as opposed to an aqueous phase. With most styles of packing, if the organic phase is the continuous phase with metal packing, poor mass transfer and poor column performance are the result (compared to when the aqueous phase is present as the continuous phase).

In the present Examples, the bisimide/dianhydride exchange reaction was carried out using the following general procedure.

In a typical procedure, a reactor was charged with 4,4'-bisphenol A-bis-N-methylphthalimide (which can also include small amounts of 3,4'-bisphenol A-bis-N-methylphthalimide and 3,3'-bisphenol A-bis-N-methylphthalimide) (32.93 grams, 0.0602 mole) and phthalic anhydride (29.98 grams, 0.2024 mole). The reaction was conducted in the presence of a triethylamine (TEA) exchange catalyst, which was provided in the form of an aqueous solution having the following composition: 15.1 wt. % triethylamine, and 13.0 wt. % phthalic anhydride, with the balance being water. 23.53 grams of this aqueous solution were added to the exchange reaction. Water was used as the solvent to provide an aqueous reaction mixture having a solids content (% solids) in the range of 13 to 15%. The bisimide/dianhydride exchange reaction was carried out at 170° C. for 2 hours. For simplicity of the discussion that follows, "N-methylphthalimide" will be referred to as "PI", the "4,4'-bisphenol A-bis-N-methylphthalimide" mixture will be referred to as "BI", and the "4,4'-bisphenol A dianhydride" product will be referred to as "DA".

The above formulation can be scaled up as desired. For the following extractions, the above reaction was appropriately scaled up and supplied to an industrial extraction column.

The above-described reaction mixture was supplied to an extraction column as shown in FIG. 2. The extraction column was packed with a high specific surface area packing material (Koch Goodloe Packing). Toluene containing 5 wt % triethylamine was supplied to the bottom of the column, and the interface of the organic solvent and the aqueous reaction mixture was maintained below the top aqueous distributor, at 55% of the column height. The volume ratio of the organic solvent to the aqueous reaction mixture was 1.4:1. The extraction column was operated at a temperature range of 145 to 170° C. with the pressure range of 200 to 250 psig.

Operating the column with a lower differential pressure between two pressure indicators (refer to Figures) (indicating that there was more bulk toluene in the column and thus phase-separated toluene as a continuous phase below the aqueous phase distribution line "a") was found to improve first pass yield. Without wishing to be bound by theory it is believed that droplets, rivulets or films of aqueous phase pass through a continuous or semi-continuous organic phase, increasing the first pass yield from 72% to 82%.

The reactor outlet and the extraction outlet compositions obtained from the above-described extraction are summarized in Table 1 below. Also shown in Table 1 are results from a Comparative Example, in which an extraction was performed using a single packed extraction column, wherein the packing was Goodloe packing, and the interface level was 7%. For the Comparative Example, the exchange reaction was carried out at a PA:BI molar ratio of 4.5:1 to 5:1 at a triethylamine TEA:PA molar ratio of 2:1. Solids content (% solids) was maintained in the range of 13 to 15%. The reaction was conducted at 170° C. at a pressure of 230 psig with a residence time of 1 hour. The aqueous feed was fed to the top of the packed extraction column, and toluene containing 5 weight percent (wt %) TEA was fed to the bottom of extraction column. The aqueous feed composition entering the extraction column was 45 mol % dianhydride as triethylammonium salts, 40 mol % IA as triethylammonium salts, and 15 mol % BI, all based on BI mole equivalents used in the reaction. Extraction was carried out with a temperature range of 145 to 170° C. with the pressure range of 200 to 250 psig.

From Table 1, it is evident that the present method enables improved extraction efficiency compared to a typical extraction process. In particular, the amount of DA and IA extracted according to Example 1 was 82.9 mole percent, compared to 72% for Comparative Example 1.

TABLE 1

| | Component | Reactor Feed (Mole Percent) | Reactor Outlet (Mole Percent) | Extraction (Mole Percent) |
|---|---|---|---|---|
| Example 1 | BI | 100 | 15 | 18.1 |
| | DA | 0 | 45 | 80.3 |
| | IA | 0 | 40 | 1.6 |
| Comparative Example 1 | BI | 100 | 15 | 28 |
| | DA | 0 | 45 | 69.5 |
| | IA | 0 | 40 | 2.5 |

The present inventors further determined that imide-anhydride content can be varied by adjusting the location of the organic/aqueous interface, as well as the temperature of the organic phase entering the column. The results are summarized below in Table 2, where "Interface Level" is given in percent based on the total height of the column, and the toluene temperature is given in degrees Celsius (° C.). The amount of imide anhydride (IA) for each interface level and temperature is given in weight percent, based on the total amount of imide anhydride and dianhydride.

It was found that allowing the organic solvent stream to enter into the bottom of the column through a modified distributor line resulted in the organic/aqueous interface to be manipulated to a desired height in the column. The modified distributor line was configured such that the organic stream entered through the aqueous phase in the form of droplets, films, rivulets, and the like, or a combination thereof, at the bottom of the column.

In Table 2 below, "Normal Toluene Distribution Line Configuration" refers to the configuration depicted in FIG. 1. "Modified Toluene Distribution Line Configuration" refers to the configuration depicted in FIG. 2. "Capacity" refers to the total flow into the column (e.g., flow of the combined aqueous and organic streams) per unit area. "CE" indicates a Comparative Example, and "E" indicates an Example according to the present disclosure.

TABLE 2

| Example | Temp. (° C.) | Toluene Distribution Line Configuration | % Height | Mole % IA in DA | % Conversion | Capacity (normalized) |
|---|---|---|---|---|---|---|
| CE2 | 165 | Normal | 7 | 2.5 | 72 | 100 |
| CE3 | 165 | Modified | 7 | 3.5 | 75 | 70 |
| E2 | 165 | Modified | 27 | 3.43 | 80 | 100 |
| E3 | 165 | Modified | 40 | 2.94 | 80 | 100 |
| E4 | 165 | Modified | 55 | 2.6 | 80 | 100 |
| CE4 | 155 | Normal | 7 | 2.5 | 72 | 100 |
| CE5 | 155 | Modified | 7 | >3.5 | 75 | 70 |
| E5 | 155 | Modified | 27 | 3.1 | 80 | 100 |
| E6 | 155 | Modified | 40 | 2.86 | 80 | 100 |
| E7 | 155 | Modified | 55 | 2.31 | >80 | >100 |
| CE6 | 145 | Normal | 7 | 2.5 | 72 | 100 |
| CE7 | 145 | Modified | 7 | >3.5 | 75 | 70 |
| E8 | 145 | Modified | 27 | 2.86 | 80 | 100 |
| E9 | 145 | Modified | 40 | 2.3 | >80 | >100 |
| E10 | 145 | Modified | 55 | 2.21 | 82 | >>100 |

It can be desirable to control the IA content to 3% or less. As can be seen in Table 2, the present inventors have determined various parameters which enable this IA level. Furthermore, it can be seen from Table 2 that overall conversion to dianhydride can be increased to 80% or greater when extraction is carried out according to the present disclosure. Additionally, the comparative example show that simply modifying the toluene distribution line but maintaining the interface level of 7% of the height of the column does not provide the desired effect. Modifying the toluene distribution line configuration but maintaining the interface level at a column height of 7% (as in comparative examples CE3, CE5 and CE7) improved the conversion only slightly (75% compared to 72% in CE2, CE4 and CE6), increased the amount of imide anhydride to 3.5% or greater, and significantly reduced the plant capacity. In contrast, the combination of the modified toluene distribution line with the desired interface level provide improved conversion, reduced imide anhydride content, and improve capacity.

This disclosure further encompasses the following aspects.

Aspect 1: A method for producing an aromatic dianhydride, the method comprising: reacting an aromatic diimide with a substituted or unsubstituted phthalic anhydride in an aqueous medium in the presence of an amine exchange catalyst under conditions effective to provide an aqueous reaction mixture comprising an N-substituted phthalimide, an aromatic tetraacid salt, and at least one of an aromatic triacid salt and an aromatic imide diacid salt, wherein the reacting is at a reaction temperature that is 140 to 250° C. and a reaction pressure of 1.13 to 2.16 MPa, (150 to 300 psig), preferably 1.48 to 1.82 MPa (200 to 250 psig); removing the phthalimide from the aqueous reaction mixture by extracting the aqueous reaction mixture with an organic solvent; and converting the aromatic tetraacid salt to the corresponding aromatic dianhydride; wherein the extracting is in an extraction column comprising a metal packing material having a specific surface area of greater than 1500 square meters per cubic meter; wherein extracting the aqueous reaction mixture comprises passing a dispersed phase comprising the aqueous reaction mixture through a continuous phase comprising the organic solvent; and wherein the extracting is in an extraction column having an interface between the aqueous reaction mixture and the organic solvent that is at a level that is 14 to 85% of the height of the extraction column packing.

Aspect 2: The method of aspect 1, wherein the high specific surface area packing material has a specific surface area of 1970 to 16400 square meters per cubic meter.

Aspect 3: The method of aspect 1 or 2, wherein the interface between the aqueous reaction mixture and the organic solvent in the extraction column is at a level that is 40 to 75%, or 45 to 65%, or 50 to 60% of the height of the extraction column.

Aspect 4: The method of any of aspects 1 to 3, wherein the aromatic dianhydride is obtained in a first pass yield of at least 75%, preferably at least 80%.

Aspect 5: The method of any of aspects 1 to 4, wherein the temperature of the organic solvent entering the extraction column is 145 to 165° C.

Aspect 6: The method of any of aspects 1 to 5, wherein the imide anhydride is present in an amount of less than 3 weight percent, preferably less than 2.6 weight percent, based on the total weight of the imide anhydride and the aromatic dianhydride.

Aspect 7: The method of any of aspects 1 to 6, wherein the substituted or unsubstituted phthalic anhydride comprises phthalic anhydride, 3-halophthalic anhydride, 4-halophthalic anhydride, 3-nitrophthalic anhydride, 4-nitrophthalic anhydride, or a combination comprising at least one of the foregoing, preferably phthalic anhydride; and wherein the exchange catalyst comprises a ($C_{1-20}$ alkyl)-substituted amine, preferably a tri($C_{1-20}$ alkyl)amine, more preferably triethylamine.

Aspect 8: The method of any one or more of aspects 1 to 7, wherein the initial molar ratio of phthalic anhydride to aromatic diimide is 4:1 to 20:1, or 4:1 to 10:1, or 4:1 to 8:1, or 4:1 to 5.5:1.

Aspect 9: The method of any one or more of aspects 1 to 8, wherein the initial molar ratio of amine exchange catalyst to the phthalic anhydride is 1:1 to 2:1.

Aspect 10: The method of any one or more of aspects 1 to 9, wherein the aqueous reaction mixture further comprises at least one of the aromatic diimide and the substituted or unsubstituted phthalic anhydride.

Aspect 11: The method of any one or more of aspects 1 to 10 wherein the aromatic diimide comprises 4,4'-bisphenol A-bis-N-methylphthalimide, 3,4'-bisphenol A-bis-N-methylphthalimide, 3,3'-bisphenol A-bis-N-methylphthalimide, or a combination comprising at least one of the foregoing; and the aromatic dianhydride comprises 4,4'-bisphenol A-bis-dianhydride, 3,4'-bisphenol A-bis-dianhydride, 3,3'-bisphenol A-bis-dianhydride, or a combination comprising at least one of the foregoing.

Aspect 12: The method of any one or more of aspects 1 to 11, wherein the organic solvent comprises toluene, xylene, chlorobenzene, ortho-dichlorobenzene, or a combination comprising at least one of the foregoing.

Aspect 13: The method of any one or more of aspects 1 to 12, wherein the volumetric ratio of the organic solvent to the aqueous reaction mixture is 1:1 to 3:1.

Aspect 14: The method of any one or more of aspects 1 to 13, wherein the extracting provides an extracted aqueous stream comprising the aromatic tetraacid salt and optionally the aromatic triacid salt, the aromatic imide-diacid salt, a substituted or unsubstituted phthalic acid salt, or a combination comprising at least one of the foregoing; and an organic stream comprising the organic solvent, N-substituted phthalimide, and optionally residual aromatic diimide.

The compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

All ranges disclosed herein are inclusive of the endpoints, and the endpoints are independently combinable with each other. "Combinations" is inclusive of blends, mixtures, alloys, reaction products, and the like. The terms "first," "second," and the like, do not denote any order, quantity, or importance, but rather are used to distinguish one element from another. The terms "a" and "an" and "the" do not denote a limitation of quantity, and are to be construed to cover both the singular and the plural, unless otherwise indicated herein or clearly contradicted by context. "Or" means "and/or" unless clearly stated otherwise. Reference throughout the specification to "some embodiments", "an embodiment", and so forth, means that a particular element described in connection with the embodiment is included in at least one embodiment described herein, and may or may not be present in other embodiments. In addition, it is to be understood that the described elements may be combined in any suitable manner in the various embodiments.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

Compounds are described using standard nomenclature. For example, any position not substituted by any indicated group is understood to have its valency filled by a bond as indicated, or a hydrogen atom. A dash ("—") that is not between two letters or symbols is used to indicate a point of attachment for a substituent. For example, —CHO is attached through carbon of the carbonyl group.

As used herein, the term "hydrocarbyl", whether used by itself, or as a prefix, suffix, or fragment of another term, refers to a residue that contains only carbon and hydrogen. The residue can be aliphatic or aromatic, straight-chain, cyclic, bicyclic, branched, saturated, or unsaturated. It can also contain combinations of aliphatic, aromatic, straight chain, cyclic, bicyclic, branched, saturated, and unsaturated hydrocarbon moieties. However, when the hydrocarbyl residue is described as substituted, it may, optionally, contain heteroatoms over and above the carbon and hydrogen members of the substituent residue. Thus, when specifically described as substituted, the hydrocarbyl residue can also contain one or more carbonyl groups, amino groups, hydroxyl groups, or the like, or it can contain heteroatoms within the backbone of the hydrocarbyl residue. The term "alkyl" means a branched or straight chain, unsaturated aliphatic hydrocarbon group, e.g., methyl, ethyl, n-propyl, i-propyl, n-butyl, s-butyl, t-butyl, n-pentyl, s-pentyl, and n- and s-hexyl. "Alkenyl" means a straight or branched chain, monovalent hydrocarbon group having at least one carbon-carbon double bond (e.g., ethenyl (—HC=CH$_2$)). "Alkoxy" means an alkyl group that is linked via an oxygen (i.e., alkyl-O—), for example methoxy, ethoxy, and sec-butyloxy groups. "Alkylene" means a straight or branched chain, saturated, divalent aliphatic hydrocarbon group (e.g., methylene (—CH$_2$—) or, propylene (—(CH$_2$)$_3$—)). "Cycloalkylene" means a divalent cyclic alkylene group, —C$_n$H$_{2n-x}$, wherein x is the number of hydrogens replaced by cyclization(s). "Cycloalkenyl" means a monovalent group having one or more rings and one or more carbon-carbon double bonds in the ring, wherein all ring members are carbon (e.g., cyclopentyl and cyclohexyl). "Aryl" means an aromatic hydrocarbon group containing the specified number of carbon atoms, such as phenyl, tropone, indanyl, or naphthyl. "Arylene" means a divalent aryl group. "Alkylarylene" means an arylene group substituted with an alkyl group. "Arylalkylene" means an alkylene group substituted with an aryl group (e.g., benzyl). The prefix "halo" means a group or compound including one more of a fluoro, chloro, bromo, or iodo substituent. A combination of different halo groups (e.g., bromo and fluoro), or only chloro groups can be present. The prefix "hetero" means that the compound or group includes at least one ring member that is a heteroatom (e.g., 1, 2, or 3 heteroatom(s)), wherein the heteroatom(s) is each independently N, O, S, Si, or P. "Substituted" means that the compound or group is substituted with at least one (e.g., 1, 2, 3, or 4) substituents that can each independently be a $C_{1-9}$ alkoxy, a $C_{1-9}$ haloalkoxy, a nitro (—NO$_2$), a cyano (—CN), a $C_{1-6}$ alkyl sulfonyl (—S(=O)$_2$-alkyl), a $C_{6-12}$ aryl sulfonyl (—S(=O)$_2$-aryl)a thiol (—SH), a thiocyano (—SCN), a tosyl (CH$_3$C$_6$H$_4$SO$_2$—), a $C_{3-12}$ cycloalkyl, a $C_{2-12}$ alkenyl, a $C_{5-12}$ cycloalkenyl, a $C_{6-12}$ aryl, a $C_{7-13}$ arylalkylene, a $C_{4-12}$ heterocycloalkyl, and a $C_{3-12}$ heteroaryl instead of hydrogen, provided that the substituted atom's normal valence is not exceeded. The number of carbon atoms indicated in a group is exclusive of any substituents. For example —CH$_2$CH$_2$CN is a $C_2$ alkyl group substituted with a nitrile.

While particular embodiments have been described, alternatives, modifications, variations, improvements, and substantial equivalents may arise to applicants or others skilled in the art. Accordingly, the appended claims as filed and as they may be amended are intended to embrace all such alternatives, modifications variations, improvements, and substantial equivalents.

What is claimed is:

1. A method for producing an aromatic dianhydride, the method comprising:
   reacting an aromatic diimide with a substituted or unsubstituted phthalic anhydride in an aqueous medium in the presence of an amine exchange catalyst under conditions effective to provide an aqueous reaction mixture comprising an N-substituted phthalimide, an aromatic tetraacid salt, and at least one of an aromatic triacid salt and an aromatic imide diacid salt, wherein the reacting is at a reaction temperature that is 140 to 250° C. and a reaction pressure of 1.13 to 2.16 MPa;
   removing the N-substituted phthalimide from the aqueous reaction mixture by extracting the aqueous reaction mixture with an organic solvent; and
   converting the aromatic tetraacid salt to the corresponding aromatic dianhydride;
   wherein the extracting is in an extraction column comprising a metal packing material having a specific surface area of greater than 1500 square meters per cubic meter;
   wherein extracting the aqueous reaction mixture comprises passing a dispersed phase comprising the aqueous reaction mixture through a continuous phase comprising the organic solvent; and
   wherein an interface between the aqueous reaction mixture and the organic solvent in the extraction column is at a level that is 14 to 85% of the height of the extraction column.

2. The method of claim 1, wherein the metal packing material has a specific surface area of 1970 to 16400 square meters per cubic meter.

3. The method of claim 1, wherein the interface between the aqueous reaction mixture and the organic solvent in the extraction column is at a level that is 40 to 75% of the height of the extraction column.

4. The method of claim 1, wherein the aromatic dianhydride is obtained in a first pass yield of at least 75%.

5. The method of claim 1, wherein the temperature of the organic solvent entering the extraction column is 145 to 165° C.

6. The method of claim 1, wherein converting the aromatic tetraacid salt provides a product mixture comprising the corresponding aromatic dianhydride and an aromatic imide-anhydride, wherein the aromatic imide-anhydride is present in an amount of less than 3 weight percent, based on the total weight of the imide anhydride and the aromatic dianhydride.

7. The method of claim 1,
   wherein the substituted or unsubstituted phthalic anhydride comprises phthalic anhydride, 3-halophthalic anhydride, 4-halophthalic anhydride, 3-nitrophthalic anhydride, 4-nitrophthalic anhydride, or a combination comprising at least one of the foregoing; and
   wherein the exchange catalyst comprises a ($C_{1-20}$ alkyl)-substituted amine.

8. The method of claim 1, wherein the initial molar ratio of substituted or unsubstituted phthalic anhydride to aromatic diimide is 4:1 to 20:1.

9. The method of claim 1, wherein the initial molar ratio of amine exchange catalyst to the substituted or unsubstituted phthalic anhydride is 1:1 to 2:1.

10. The method of claim 1, wherein the aqueous reaction mixture further comprises at least one of the aromatic diimide and the substituted or unsubstituted phthalic anhydride.

11. The method of claim 1 wherein
- the aromatic diimide comprises 4,4'-bisphenol A-bis-N-methylphthalimide, 3,4'-bisphenol A-bis-N-methylphthalimide, 3,3'-bisphenol A-bis-N-methylphthalimide, or a combination comprising at least one of the foregoing; and
- the aromatic dianhydride comprises 4,4'-bisphenol A-bis-dianhydride, 3,4'-bisphenol A-bis-dianhydride, 3,3'-bisphenol A-bis-dianhydride, or a combination comprising at least one of the foregoing.

12. The method of claim 1, wherein the organic solvent comprises toluene, xylene, chlorobenzene, ortho-dichlorobenzene, or a combination comprising at least one of the foregoing.

13. The method of claim 1, wherein the volumetric ratio of the organic solvent to the aqueous reaction mixture is 1:1 to 3:1.

14. The method of claim 1, wherein the extracting provides
- an extracted aqueous stream comprising the aromatic tetraacid salt and optionally the aromatic triacid salt, the aromatic imide-diacid salt, a substituted or unsubstituted phthalic acid salt, or a combination comprising at least one of the foregoing; and
- an organic stream comprising the organic solvent, the N-substituted phthalimide, and optionally residual aromatic diimide.

* * * * *